United States Patent [19]
Aldous et al.

[11] Patent Number: 5,514,692
[45] Date of Patent: May 7, 1996

[54] SUBSTITUTED QUINOLINE DERIVATIVES USEFUL AS ANTIPICONAVIRAL AGENTS

[75] Inventors: David J. Aldous, Glenmore; Thomas R. Bailey, Phoenixville; Guy D. Diana, Pottstown; Gee-Hong Kuo, Blue Bell; Theodore J. Nitz, Pottstown; Michael Reuman, Audubon, all of Pa.

[73] Assignee: Sterling Winthrop Inc., New York, N.Y.

[21] Appl. No.: 449,463

[22] Filed: May 24, 1995

Related U.S. Application Data

[62] Division of Ser. No. 312,724, Sep. 27, 1994.

[51] Int. Cl.$^6$ .................. A61K 31/47; C07D 401/04
[52] U.S. Cl. .................. 514/314; 546/153; 546/155; 546/157; 546/159; 546/162; 546/167; 514/312; 514/313
[58] Field of Search ............... 546/167; 514/314

[56] References Cited

U.S. PATENT DOCUMENTS 5,436,247  7/1995  Sohda et al. .................. 514/314

*Primary Examiner*—Johann Richter
*Assistant Examiner*—Laura L. Stockton
*Attorney, Agent, or Firm*—Paul E. Dupont; William J. Davis

[57] ABSTRACT

The invention discloses compounds of the formula

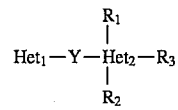

wherein, $Het_1$ is chosen from the group consisting of substituted or unsubstituted furyl, oxazolyl, isoxazolyl, oxadiazolyl, tetrazolyl, thiadiazolyl Y is an alkylene bridge of 3 to 9 carbon atoms.

$Het_2$ is quinolyl quinolyl substituted by $R_1$ and $R_2$;

$R_1$ and $R_2$ are each individually chosen from hydrogen, halo, alkyl, alkenyl, amino, alkylthio, hydroxy, hydroxyalkyl, alkoxyalkyl, alkylthioalkyl, alkylsulfinyl alkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;

$R_3$ is alkyltetrazolyl, or substituted or unsubstituted heterocyclyl chosen from benzoxazolyl, benzathiazolyl, thiadiazolyl, imidazolyl, dihydroimidazolyl, oxazolyl, thiazolyl, oxadiazolyl, pyrazolyl, isoxazolyl, isothiazolyl, furyl, triazolyl, tetrazolyl, thiophenyl the N-oxide thereof or a pharmaceutically acceptable acid addition salt thereof are effective antipicornaviral agents.

18 Claims, No Drawings

SUBSTITUTED QUINOLINE DERIVATIVES USEFUL AS ANTIPICONAVIRAL AGENTS

This application is a division of application Ser. No. 08/312,724, filed on Sep. 27, 1994.

BACKGROUND OF THE INVENTION

1. Field of the Invention

This invention relates to antipicornaviral compounds and their uses.

2. Summary of the Invention

We have found that compounds of Formula I are effective antipicornaviral agents. Accordingly, the present invention relates to compounds of the formula;

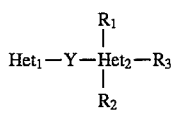

wherein, $Het_1$ is chosen from the group consisting of furyl, oxazolyl, isoxazolyl, oxadiazolyl, tetrazolyl, thiadiazolyl, pyridyl, pyrimidyl, pyridazyl, pyrazyl or any of these substituted with alkyl, alkoxy, hydroxy, cycloalkyl, hydroxyalkyl, hydroxyhaloalkyl, alkoxyalkyl, hydroxyalkoxy, alkyl thioalkyl, alkanoyl alkanoyloxy, alkylsulfinyl alkyl, alkylsulfonylalkyl amino alkyl, alkylaminoalkyl, dialkylaminoalkyl, alkoxycarbonyl, carboxy cyanomethyl, fluoroalkyl or halo.

Y is an alkylene bridge of 3 to 9 carbon atoms.

$Het_2$ is quinolyl, benzofuranyl, indolyl, benothiazolyl or benzoxazolyl; or these substituted by $R_1$ and $R_2$.

$R_1$ and $R_2$ are each individually chosen from hydrogen, halo, alkyl, alkenyl, amino, alkylthio, hydroxy, hydroxyalkyl, alkoxyalkyl, alkylthioalkyl, alkylsulfinyl alkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;

$R_3$ is alkoxycarbonyl, alkyltetrazolyl, phenyl or heterocyclyl chosen from benzoxazolyl, benzathiazolyl, thiadiazolyl, imidazolyl, dihydroimidazolyl, oxazolyl, thiazolyl, oxadiazolyl, pyrazolyl, isoxazolyl, isothiazolyl, furyl, triazolyl, tetrazolyl, thiophenyl, pyridyl, pyrimidinyl, pyrazinyl, pyridazinyl or any of the above substituted with alkyl, halo, alkoxyalkyl, cycloalkyl, haloalkyl, hydroxyalkyl, alkoxy, hydroxy, furyl, or thienyl or fluoroalkyl the N-oxide thereof or a pharmaceutically acceptable acid addition salt thereof.

The invention also relates to compositions for combating picornaviruses comprising an antipicornavirally effective amount of a compound of Formula I with a suitable carrier or diluent, and to methods of combating plcornaviruses therewith, including the systemic treatment of picornaviral infections in a mammalian host.

DETAILED DESCRIPTION OF PREFERRED EMBODIMENTS

Compounds of Formula I are useful as antipicornaviral agents, and are further described hereinbelow.

Alkyl and alkoxy refer to aliphatic radicals, including branched radicals, of from one to five carbon atoms. Thus the alkyl moiety of such radicals include, for example methyl, ethyl, propyl, isopropyl, n-butyl, sec-butyl, t-butyl, pentyl and the like. Alkoxy refers to alkyloxy, such as methoxy, pentoxy and the like.

Cycloalkyl means an alicyclic radical having from three to seven carbon atoms as illustrated by cyclopropyl, cyclobutyl, cyclopentyl, cycloheptyl, and cyclohexyl; and Halo means bromo, chloro, iodo or fluoro.

The general term Heterocyclyl or Het refers to a 5 or 6 membered carbon based heterocycle radical (monocyclic heterocycles), having from one to about four nitrogen atoms and/or one oxygen or sulfur atom, provided that no two oxygen and/or sulfur atoms are adjacent in the heterocycle, or the term can refer to 9 or 10 membered carbon based heterocycles with heteroatoms as described above (bicyclic heterocycles). Examples of monocyclic heterocycles include furyl, oxazolyl, isoxazolyl, pyrazyl, imidazolyl, thiazolyl, tetrazolyl, thienyl, pyridyl, oxadiazolyl, thiadiazolyl, triazinyl, pyrimidinyl and the like. Examples of bicyclic heterocycles include quinolyl, isoquinolyl, benzofuranyl, benzothiazolyl, benzoisoxazol, benzoxazolyl, benthiazolyl and the like.

The term heterocyclyl includes all known isomeric radicals of the described heterocycles unless otherwise specified, for example, thiadiazolyl encompasses 1,3,4-thiadiazol-2-yl, 1,2,4-thiadiazol-5-yl, and 1,2,4-thiadiazol-3-yl; thiazolyl encompasses 2-thiazolyl, 4thiazolylyl and 5-thiazolyl and the other known variations of known heterocyclyl radicals. Thus any isomer of a named heterocycle radical is contemplated. These heterocycle radicals can be attached via any available nitrogen or carbon, for example, tetrazolyl contemplates 5-tetrazolyl or tetrazolyl attached via any available nitrogen of the tetrazolyl ring; furyl encompasses furyl attached via any available carbon, etc. The preparation of such isomers are well known and well within the scope of skilled artisan in medicinal or organic chemistry.

Certain heterocycles can exist as tautomers, and the compounds as described, while not explicity mentioning each tautomeric form, are meant to embrace each and every tautomer. For example, pyridazin-6-ones and 6-hydroxypyridazines are tautomers. Thus the compounds of formula I depicted as hydroxypyridazines ($R_3$=OH) are understood to include the tautomeric pyridazinones.

In the use of the terms hydroxyalkyl and alkoxyalkyl, it is understood that the hydroxy and alkoxy groups can occur at any available position of the alkyl. Thus hydroxyalkyl and alkoxyalkyl include, for example, hydroxymethyl, 1-hydroxyethyl, 2-hydroxyethyl, 2-hydroxypropyl, 2-hydroxyisopropyl, 2-, 3-, 4- and 5-hydroxypentyl and the like; alkoxy refers to the corresponding alkyl ethers thereof.

In the use of the term hydroxyalkoxy, it is understood that the hydroxy group can occur at any available position of alkoxy other than the C-1 (geminal) position. Thus hydroxyalkoxy includes, for example, 2-hydroxyethoxy, 2-hydroxypropoxy, 2-hydroxyisopropoxy, 5-hydroxypentoxy and the like.

Alkylene refers to a linear or branched divalent hydrocarbon radical of from 1 to about 5 carbon atoms such as methylene, 1,2-ethylene, 1,3-propylene, 1,4-butylene, 1,5-pentylene, 1,4-(2-methyl)butylene and the like. Alkylene also includes the above group having an alkene or alkyne linkage therein.

Halogen refers to the common halogens fluorine, chlorine, bromine and iodine.

As used herein, the term haloalkyl refers to a halo substituted alkyl, such as fluoroalkyl, chlorofluoroalkyl, bromochloroalkyl, bromofluoroalkyl, bromoalkyl, iodoalkyl, chloroalkyl and the like where the haloalkyl has one or more than one of the same or different halogens substituted for a hydrogen. Examples of haloalkyl include chlorodifluoromethyl, 1-chloroethyl, 2,2,2-trichloroethyl, 1,1-dichloroethyl, 2-chloro, 1,1,2,2-tetrafluoroethyl, bromoethyl and the like.

As used herein the term fluoroalkyl is a preferred subclass of haloalkyl, and refers to fluorinated and perfluorinated alkyl, including, for example, fluoromethyl, difluoromethyl, trifluoromethyl, 2,2,2-trifluoroethyl, 1,2-difluoroethyl, 1-fluoroethyl, 1,1-difluoroethyl, 1,1,2,3-tetrafluorobutyl and the like.

Throughout the specification the term Z refers to a leaving group. The definition of leaving group is well known in the art and includes for example alkoxy, trityl, benzyl, halo and the like.

The term X refers to a group which can be displaced by or elaborated into a heterocyclic group. The skilled artisan will know how to choose X based upon the target heterocycie.

The compounds of Formula I wherein $Het_1$, $Het_2$ or $R_3$ is a basic nitrogen containing heterocycle are sufficiently basic to form acid addition salts and are useful both in the free base form and the form of acid-addition salts, and both forms are within the purview of the invention. The acid-addition salts are, in some cases, a more convenient form for use, and in practice the use of the salt form inherently amounts to the use of the base form. The acids which can be used to prepare the acid-addition salts include preferably those which produce, when combined with the free base, medicinally acceptable salts, that is, salts whose anions are relatively innocuous to the animal organism in medicinal doses of the salts so that the beneficial properties inherent in the free base are not vitiated by side effects ascribable to the anions. Examples of appropriate acid-addition salts include the hydrochloride, hydrobromide, sulfate, acid sulfate, maleate, citrate, tartrate, methanesulfonate, p-toluenesulfonate, dodecyl sulfate, cyclohexanesulfamate, and the like. However, other appropriate medicinally acceptable salts within the scope of the invention are those derived from other mineral acids and organic acids. The acid-addition salts of the basic compounds can be prepared by dissolving the free base in aqueous alcohol solution containing the appropriate acid and isolating the salt by evaporating the solution, or by reacting the free base and an acid in an organic solvent, in which case the salt separates directly, is precipitated with a second organic solvent, or by concentration of the solution or by any one of several other known methods. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed only for purposes of purification or identification, or when it is used as an intermediate in preparing a medicinally acceptable salt by ion exchange procedures.

The N-oxides of the structures of the compounds of the invention were established by the mode of synthesis, by elemental analysis, or by infrared, ultraviolet, nuclear magnetic resonance or mass spectroscopy. The identity and homogeneity of the products were assessed by thin layer chromatography (TLC) or gas-liquid chromatography (GLC) or other art accepted means.

As described herein a noninteracting solvent can be N-methyl pyrrolidinone (NMP), methylene chloride ($CH_2Cl_2$), tetrahydrofuran (THF), benzene or any other solvent that will not take part in the reaction. In a preferred method, the preparation of compounds of the invention is done in dried solvents under an inert atmosphere. Certain reagents used in example preparations are specified by abbreviation: triphenylphosphine (TPP), m-chloroperbenzoic acid (MCPBA) triethylamine (TEA), diisopropylethylamine (DIPEA), and diethyl azodicarboxylate (DEAD). Ether is diethyl ether unless otherwise specified.

Preferred methods of preparing compounds of Formula I are shown by the four schemes below:

I. $Het_2$ = Benzofuranyl

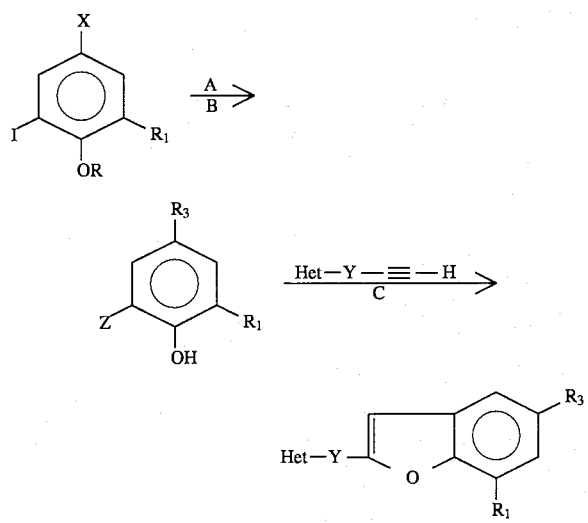

Reactions referred to are;

A=$R_3$ Het precursor (X) displacement or elaboration of X (to $R_3$)

B=any known deprotection of phenol (removal of R from OR)

C=any known etherification reaction

II. $Het_2$ = Benzothiazolyl or benzoxazolyl

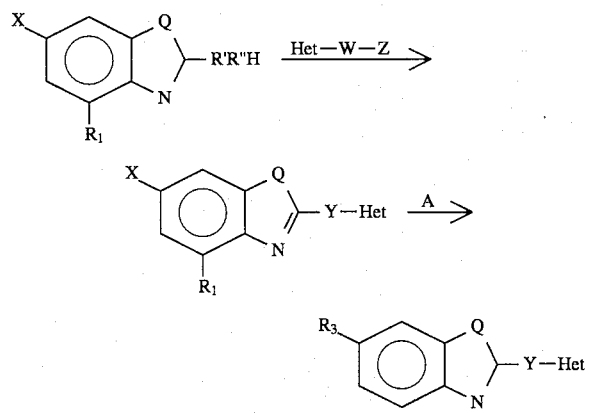

wherein:

W=Y, less the terminal CR'R''; (R' and R'' are hydrocarbon radicals which represent branching in the broader term Y)

Z=halogen or leaving group; and

Q=S or O.

Reactions referred to are;

A=$R_3$ displacement of X or elaboration of X to $R_3$.

III. $Het_2$ = quinolyl

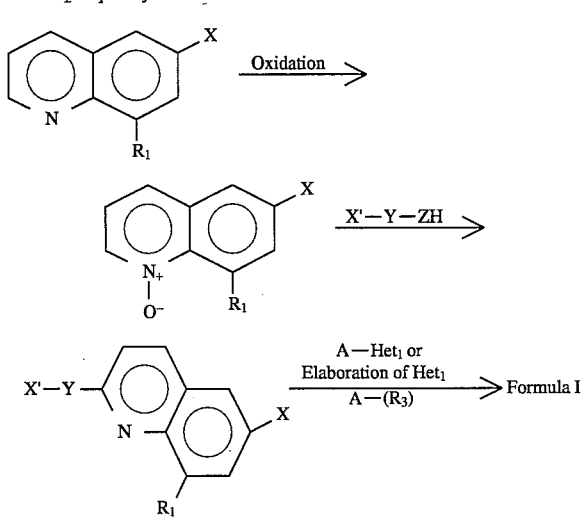

Z is a leaving group (e.g. halo, trityl etc.)

X or X' is a $Het_1$ precursor; alkylene, cyano, etc., which is later elaborated, by known methods to $Het_1$ or alternatively is a group of which can be displaced by a heterocycle using known methods.

Reactions referred to are;

A=elaboration of $Het_1$ and/or $R_3$ from X or X'; or displacement of X or X" by $R_3$/$Het_1$ as appropriate.

IV. $Het_2$ = indolyl

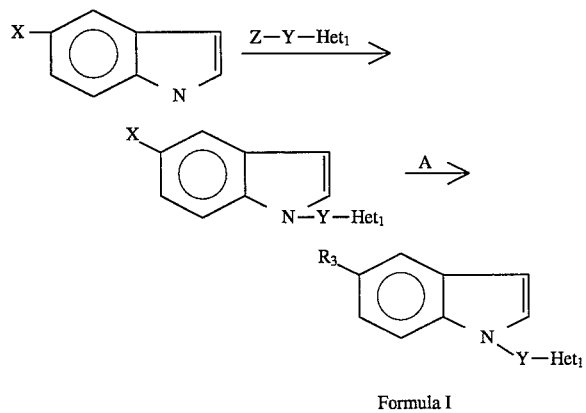

Formula I wherein Z is a leaving group;

Reaction A refers to the preparation of $R_3$ (as above).

It will be appreciated that neither the timing of the elaboration (or substitution) of the heterocyclic substituents, nor the order of assembly of the intermediates is crucial to the successful synthesis of compounds of Formula I. However, the skilled artisan will immediately recognize that the synthesis may be more successful when performing steps in a certain order so as to avoid undesirable side products. When preparing compounds of formula I it may be advantageous to arrange the order of synthesis so that yields are maximized. For example, the skilled artisan will appreciate that certain of the $R_3$ or $Het_1$ heterocycles disclosed herein are susceptible to such undesired reactions. This susceptibility may cause undesired side products caused by elaborating certain of these heterocycles during the synthesis. The susceptibility to nucleophiles is also a consideration when determining when each heterocycle is to be elaborated, if the Y-$Het_2$ moiety has already been formed, but has not had $Het_1$ or $R_3$ elaborated yet. Thus elaboration of heterocycles which are nucleophile-susceptible may be delayed until late in the synthesis. In such cases it may be advantageous to prepare a functionalized precursor in the position of the bet such as ester, amide, cyano group. For example a preferred method of preparing a compound wherein $Het_1$ is 2-alkyl tetrazolyl is to prepare the corresponding cyanoalkoxyphenylheterocycle or cyanoalkoxyphenyl heterocycle precursor. Other processes will be understood by analogy. A preferred method of preparing compounds of formula I wherein $R_3$ is trifluoromethyl oxadiazolyl, is to elaborate the oxadiazolyl moiety last from a cyano group, to avoid undesired side reactions. As a further example, when $Het_1$ is triazines (and any other π deficient ring) this ring is elaborated after formation of the $R_3$-$Het_2$-Y-moiety. These considerations are well understood by the skilled artisan and are spelled out in detail in Katritzky Comprehensive Heterocyclic Chemistry (1985).

Certain Z-Y-$Het_1$ are easily attached via reaction of the formed and optionally functionalized $Het_2$ heterocycles and a reactive end of the molecule.

For example, a preferred method of preparation of molecules where $Het_1$ is imidazole comprises the formation of a halo-Y-($R_3$) $Het_2$ moiety, then reacting it with an appropriately functionalized imidazole. For example, a tin-imidazole species may be reacted with a terminally unsaturated -Y-($R_3$)$Het_2$ species.

In a preferred method, the compound of Formula I can be prepared from an appropriate X $Het_2$-Y-$Het_1$ species, wherein the X is the desired $R_3$ heterocycle precursor described above. For example, starting materials where X is cyano are known in the art and the Formula I precursors can be prepared from known materials using methods well known in the art. It will be understood that when applied to quinolines, indoles, benzofurans, benzothiazoles, benzoxazoles, or other $Het_2$ precursors, the method will produce an intermediate which is then useful in preparing the compound of Formula I when reacted with the appropriate ω-$Het_1$-Y moiety. The $R_3$ heterocycle may be elaborated as a final step when preparing a compound of Formula I. The choice of suitable substituents for use as X will depend upon the $R_3$ heterocycle sought in the final product. For example, where $R_3$ is 1, 2, 4-oxadiazolyl

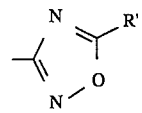

compounds are prepared from the appropriate nitrile compound (X=cyano) by reaction with hydroxylamine hydrochloride in a noninteracting solvent, preferably pyridine or an alkanol, for example, methanol, ethanol, n-butanol, and the like, in the presence of a base, such as potassium carbonate, at a temperature between ambient temperature and the boiling point of the solvent. The product thus obtained is then reacted with an acid anhydride of formula (R'CO)$_2$O, (where R' is alkyl, haloalkyl); with R' appearing as a substituent on $R_3$ of the product. For example trifluoroacetic anyhdride, or acetic anhydride, yield trifluormethyl or methyl as R' respectively. The product is a compound of formula I where the starting material is $Het_1$-Y- ($R_1$, $R_2$)$Het_2$-X (and alternatively a $Het_2$ oxadiazole, where the starting material is $Het_2$-X).

Where the compound of formula I has the same heterocyle for $Het_1$ and $R_3$ these heterocycles may be elaborated at the same time from suitable precursors by adding the appropriate excess of reactants, and using the standard reaction conditions. Alternatively $Het_1$ and $R_3$ may be substituted onto the molecule by displacing a leaving group such as X or Z described above.

Thus by judicious choice of reactants one can prepare any of the compounds of Formula I, by several different routes.

Simple chemical transformations which are conventional and well known to those skilled in the art of chemistry can be used for effecting changes in functional groups in the compounds of the invention. For example, acylation of hydroxy- or amino-substituted species to prepare the corresponding esters or amides, respectively; alkylation of aromatic and heterocyclic substituents; cleavage of alkyl or benzyl ethers to produce the corresponding alcohols or phenols; and hydrolysis of esters or amides to produce the corresponding acids, alcohols or amines, preparation of anhydrides, acid halides, aldehydes, simple aromatic alkylation and the like as desired can be carried out.

Moreover, it will be appreciated that obtaining the desired product by some reactions will be better facilitated by blocking or rendering certain functional groups unreactive. This practice is well recognized in the art, see for example, Theodora Greene, Protective Groups in Organic Synthesis (1991). Thus when reaction conditions are such that they can cause undesired reactions with other parts of the molecule, the skilled artisan will appreciate the need to protect these reactive regions of the molecule and act accordingly.

Starting materials used to prepare the compounds of Formula I are commercially available, known in the art, or prepared by known methods. Many of the preparations of starting materials herein are incorporated by reference from the patent literature. The following examples are provided to show the practitioner how to make compounds of Formula I, not to limit the claims.

Working Examples

Example 1

1a. To a solution of 10.7 g of 3,5-dimethylisoxazole and 150 mL of dry THF at −78° C. was added 11.5 mL of 10 M n-buLi. After 10 minutes the orange solution was quenched with a solution of 24.1 g of 5-bromo-1-trimethylsilylpent-1-yne in 50 mL of dry ether. The mixture was allowed to warm to room temperature and poured into water, then extracted with ether. The ether phase was washed with water, dried over sodium sulfate, concentrated and filtered through silica gel providing 31.1 g (82%) of the product is a pale yellow oil.

1b. The TMS alkyne isoxazole prepared above was taken up in 150 mL of ether and 95 mL of 1.1 M tetrabutylammoniumfluoride solution in THF was added. The dark brown mixture was stirred at room temperature under nitrogen for 2 hours. The mixture was poured into water and the ether layer was washed twice with water and dried over potassium carbonate. Concentration in vacuo and flash filtration over silica gel provided 13.5 g (91%) of a red brown oil, used without further purification.

1c. 4.8 g of 3-(3-iodo-4-hydroxy-5-methyl)phenyl-5-methyl-1,2,4-oxadiazole was prepared according to the method disclosed in allowed U.S. patent application No. 07/869,287, now U.S. Pat. No. 5,349,068, incorporated herein by reference (M.P. 111°–115° C.)

1d. To a suspension of the acetylene compound prepared in 1b, (1.1 g) in 10 mL THF 1.0 g of triethylamine, 0.18 g of copper iodide, was added. 2.0 g of the 4-hydroxyphenyloxadiazole produced in 1c and 0.23 g of bis(triphenylphosphinedichloro) palladium(II) was added. The resulting dark brown solution exhibited a mild exotherm and became lighter in color. The mixture was stirred at room temperature for twelve hours. Flash chomatography through silica gel provided 1.13 g of the product as a yellow oil which solidified upon standing. Recrystallization from isopropyl acetate and hexanes provided 0.5 g of the product as a fluffy white solid (M.P. 75°–77° C.). Formula I; $Het_1$=3-methylisoxazol-5-yl; $Het_2$=2,5-benzofuryl, $R_1$=7-methyl; $R_2$=hydrogen, $R_3$=5-methyl-1,2,4 -oxadiazolyl.

1e. The following compounds of Formula I where $Het_2$= benzofuryl; $Het_1$=3-methyl 5-isoxazolyl; $R_2$ is hydrogen and $R_1$ is in the 7 position of the benzofuranyl ring, and Y is of the formula $(CH_2)_N$ were prepared by similar methods:

| Ex. No. | N | $R_1$ | $R_3$ | M.P. |
| --- | --- | --- | --- | --- |
| 1f | 4 | H | 5-methyl-1,2,4-oxadiazolyl | 102–104 |
| 1g | 3 | $CH_3$ | 5-methyl-1,2,4-oxadiazolyl | 100–101 |
| 1h | 4 | Cl | 5-methyl-1,2,4-oxadiazolyl | 106–104 |
| 1i | 4 | $CH_3$ | 5-trifluoromethyl 1,2,4-oxadiazolyl | 63–65 |
| 1j | 5 | H | carboxy | 117–119 |
| 1k | 5 | H | 2-oxazolinyl | 63–64 |
| 1l | 4 | $CH_3$ | 2 butyl tetrazol-5-yl | 58–61 |
| 1m | 3 | $CH_3$ | 2-methyl tetrazol-5-yl | 101–103 |
| 1n | 2 | $CH_3$ | 2-methyl tetrazol-5-yl | 127–129 |
| 1o | 4 | $CH_3$ | 3-methyl-1,2,4-oxadiazolyl | 90–91 |
| 1p | 4 | $CH_3$ | 5-methyl-1,2,4-oxadiazolyl | 75–77 |
| 1q | 4 | $CH_3$ | cyano | 89–91 |

Example 2

2a. 300 mg of 5-cyano-7-methyl indole, 445 mg of (3-chloropropyl) 5-methylisoxazole, 665 mg of potassium carbonate, 300 mg of potassium iodide was combined in 4 mL of NMP. The mixture was heated under nitrogen at approximately 70° C. for approximately 48 hours. Upon cooling, ethyl acetate and water was added, the mixture extracted twice with ethyl acetate. The aqueous layer formed a white precipitate. Water was decanted and the ethyl acetate layer was combined with the precipitate, dried over magnesium sulfate, filtered and concentrated in vacuo to a brown oil. The oil was taken up in a minimal amount of methylene chloride and flash filtered over silica gel (eluting with 30% ethyl acetate and hexane). The appropriate fractions were combined, filtered, and dried, yielding 339.7 mg (64%) of a product (M.P. 101°–104° C.).

2b. The 5-cyano product obtained was then treated by the methods described in allowed U.S. patent application No. 07/869,287, to yield the corresponding compound of Formula IV. (M.P. 79°–80° C. ) (135 rag) . ($R_3$=5-trifluoromethyl-1,2,4-oxadiazol-3-yl; $R_1$=7-methyl; $R_2$=hydrogen; Y=i, 3-propylene; $Het_1$=3-methyl isoxazol-5-yl; $Het_2$=N, 5 indolyl) . The following compounds of formula I were prepared wherein Y=$(CH_2)N$; $Het_1$=3-methyl-isoxazol-5-yl; $R_2$=hydrogen, $Het_2$=N-5-indolyl; $R_1$ is in the 7 position and $R_3$ is 5-$R^1$-1,2,4-oxadiazol-3-yl:

| Ex. No. | N | $R_1$ | $R^1$ | M.P. |
| --- | --- | --- | --- | --- |
| 2c | 3 | H | CH3 | 96–97 |
| 2d | 4 | $CH_3$ | $CF_3$ | 99–100 |
| 2e | 5 | $CH_3$ | $CF_2H$ | 85–86 |
| 2f | 5 | $CH_3$ | $CF_3$ | 101–102 |
| 2g | 3 | H | $CF_2H$ | 72–73 |
| 2h | 3 | $CH_3$ | $CH_3$ | 99–100 |

-continued

| Ex. No. | N | R₁ | R¹ | M.P. |
| --- | --- | --- | --- | --- |
| 2i | 3 | H | CF₃ | 71–72 |

Example 3

3a. 1.1 g of sodium hydride was added to 100 mL of DMF. The solution was warmed to 60° C. for 40 minutes and then the DMF solution containing 4.3 g of 5(3-chloropropyl) 3-methylisoxazole was added. The mixture was stirred at 60° C. for two hours. Upon cooling the reaction mixture was concentrated in vacuo. Water and ethyl acetate was then added to the mixture and the mixture was extracted twice with ethyl acetate. The ethyl acetate layer was dried over magnesium sulfate, filtered and concentrated in vacuo, taken up in a minimal amount of methylene chloride and then chromatographed through silica gel using an ethyl acetate/hexane solution. Appropriate fractions were concentrated yielding 3.9 g, (81%) of a 5-cyano compound (M.P. 96°–97° C.).

3b. The product obtained above was reacted with tetramethyltin and bis (triphenylphosphinedichloro) palladium in DMF at 130° C. to yield a product wherein $R_1$ is methyl. (M.P. 53°–54° C.).

3c. The cyano compound is reacted by the methods described in allowed U.S. patent application No. 07/869,287, to yield the corresponding compound of Formula I wherein $R_3$ is 5-trifluoromethyl, 1,2,4-oxadiazol-3-yl, $R_1$ is methyl, $R_2$ is hydrogen, Y is 1,3-propylene, $Het_1$ is 3-methylisoxazol-3-yl, $Het_2$=1,5-indolyi(2,3-dihydro). (M.P. 77°–78° C.).

Example 4

4a. 4.87 g of 6-bromo-2,5-dimethyl benzothioazole was taken up in 100 mL of THF and the reaction mixture was placed under argon and chilled to −78° C. in a dry ice/isopropanol bath while 20 mL of 1.5 M LDA added. The mixture turned a deep red color after 10 minutes. 7.58 g of 3-(3-iodo)propyl-5-methylisoxazole was added and the cooling bath was removed. The mixture was allowed to stir until it reached room temperature. The mixture was then allowed to set overnight, and was quenched with 25 mL of water and concentrated in vacuo. The mixture was then taken up in ether and washed with water, dried over sodium sulfate and concentrated to give a red oil. This oil was filtered through a silica gel column using 1:2 ether/hexane mixture. The fractions containing the product were combined and concentrated in vacuo yielding 5.58 g (76%) of the isoxazolylalkyl benzothioazole compound.

4b. The compound prepared above was combined with 2.69 g of CuCN in 55 mL of NMP under argon and then heated to 140° C. for 20 hours. The reaction was poured onto ice, with concentrated amonium hydroxide and ether. The mixture was stirred, partitioned, and the aqueous layer was extracted several times with ether. Ether extracts were filtered through a pad of silica gel and concentrated to give an oil. The oil was chromatographed on silica gel using a 1:2 mixture of ether and hexane giving an off white solid (M.P. 105°–107° C.), giving 0.87 g of an off white solid (M.P. 105°–107° C.).

4c. The 6-cyano benzothiazole obtained above was reacted under the conditions described in allowed U.S. patent application No. 07/869,287, to yield the corresponding 6[5-methyl-i, 2,4-oxadiazole-3-yl] compound. (M.P. 77°–78° C.). (Y=1. 3-propylene, $R_1$=methyl, $R_2$=hydrogen, $R_3$=5-methyl-1, 2,4-oxadiazole-3-yl).

Example 5

5a. 50 g of MCPBA and 23.0 g of the 6-bromo-8-methylquinoline were combined in 1 L of ChCl₃ at room temperature. The solution was heated at 60° C. for 6 hours. An additional 10 g of MCPBA was added and the mixture stirred at 20° C. for 2 hours. To the stirred suspension, saturated aqueous potassium carbonate was added. The chloroform layer was washed with water and dried over sodium sulfate, filtered and concentrated to yield 26.8 g of the corresponding crude N-oxide. Recrystallization from acetonitrile provided 14.09 g of product. A second crop provided 3.13 g of the product.

5b. 4-bromobutylalkyne (0.25 M) and 35 mL of chlorotrimethylsilane were combined in 250 mL of ether. The mixture was chilled under argon in a dry ice/isopropanol bath and 25 mL of (10 M) N-butyl lithium was added dropwise and the mixture was allowed to warm to room temperature. The mixture was then filtered through a pad of silica gel to give a lightly colored oil (83%) 48.165 g.

5bc. N-oxide from 5a above and the trimethylsilane protected alkyne from 5b above was combined with magnesium and THF and sonicated. The mixture was then worked up by pouring the mixture over ice and then adding saturated ammonium chloride. The mixture was extracted with ether, dried over sodium sulfate, filtered and concentrated. The resulting material was filtered through a pad of silica gel using ether to give 7.78 g of the product which was then deprotected by conventional means.

d. 2.7 g of NCS was added to 20 mL of chilled DMF. To this mixture, 1.0 mL of aldoxime was added and the mixture was heated in a water bath of 80° C. for 10 minutes. The mixture was then cooled to room temperature and the alkyne obtained above was added. The mixture was heated to 40°–50° C. and then 2.5 mL of triethylamine and 5 mL of DMF was added dropwise. After 19 hours and the appropriate workup, 700 mg of the corresponding isoxazole compound was obtained. The 6-bromo compound was then treated with CuCN in NMP to produce a corresponding 6-cyano compound.

5e. The cyano compound was treated according to the methods of U.S. allowed application 07/869,287, to provide a compound of Formula I wherein Het is 5-methyl-l,2,4-oxadiazole-3-yl, $R_1$ is methyl, Y is 1,4-butylene (M.P. 104°–105° C.).

Example 6

It is contemplated that any of the methods disclosed in allowed application 07/869,287, incorporated herein by reference, is also useful in forming the $R_3$ heterocycle in compound of formula I. It is also contemplated that any of the $R_3$ heterocycles can be elaborated or substituted using the methods described in the patents below, each incorporated by reference. For the reader's convenience the same nomenclature conventions described herein for compounds of formula I are adhered to for phenol intermediates listed below, and a literature reference describing the known phenol is included.

| R₁ | R₂ | R₃ | Reference U.S. Pat. No. |
|---|---|---|---|
| H | H | 1,2,4-oxadiazol-2yl | 4,857,539 |
| H | H | 4,2-dimethyl-2-thiazolyl | 4,857,539 |
| H | H | 2-benzoxazolyl | 4,857,539 |
| 3,5 dichloro | | 3-furanyl | 4,857,539 |
| 3,5 dichloro | | 2-furanyl | 4,857,539 |
| 3,5 dichloro | | 2-thienyl | 4,857,539 |
| 3,5 dichloro | | 2-pyridinyl | 4,857,539 |
| 3,5 dichloro | | 1-methyl-1H-pyrrol-2yl | 4,857,539 |
| 3,5 dichloro | | 3-thienyl | 4,857,539 |
| 3,5 dichloro | | 4-pyridinyl | 4,857,539 |
| 3 nitro | H | benzothiazol-2-yl | 4,857,539 |
| H | H | 2-(4,5-dihydro-4 methyl)oxazolyl | 4,843,087 |
| 3 methyl | H | 2-oxazolyl | 4,843,087 |
| 3 bromo | H | 2-oxazolyl | 4,843,087 |
| 3,5 dimethyl | | 3-methyl-5-isoxazolyl | 4,843,087 |
| 2,6 dimethyl | | 3-methyl-5-isoxazolyl | 4,843,087 |
| H | H | 5-methyl-3-isoxazolyl | 4,942,241 |
| H | H | 4-hydroxy phenyl | (Aldrich) |
| H | H | phenyl | (Aldrich) |
| H | H | 5-ethyl-thiazol-2-yl | 5,100,893 |
| H | H | 4,5-dimethyl-thiazol-2-yl | 5,100,893 |
| H | H | 2-ethyl-thiazol-yl | 5,100,893 |
| H | H | 5-ethyl-1,3,4-thiadiazol-2-yl | 5,100,893 |
| H | 3-Cl | 3-ethyl-1,2,4-oxadiazol-5-yl | 5,100,893 |
| H | H | 3-cyclopropyl-1,2,4-oxadiazol-5-yl | 5,100,893 |
| H | H | 3-tbutyl-1,2,4-oxadiazolyl | 5,100,893 |
| H | H | 5-ethyl-1,3,4-oxadiazol-2-yl | 5,100,893 |
| H | H | 3-cyclopropyl,2,4-oxadiazol-5-yl | 5,100,893 |
| H | H | 3-ethyl-1,3,4-thiadiazol-5-yl | 5,100,893 |
| H | H | 3-(2hydroxy)propyl-1,2,4-oxadiazol-5-yl | 5,100,893 |
| H | H | 4-ethyl-3-thiazol-2-yl | 5,100,893 |
| H | H | 5-ethyl-3-thiazol-2-yl | 5,100,893 |
| 3-chloro | H | 3-ethyl-1,2,4-oxadiazol-5-yl | 5,100,893 |
| H | H | 4,5-dimethyl-3-thiazol-2-yl | 5,100,893 |
| 2-methoxy | H | 4,5dihydro oxazol-2-yl | 4,843,087 |
| 3-methoxy | H | 4,5dihydro oxazol-2-yl | 4,843,087 |
| 3-chloro | H | 4,5dihydro oxazol-2-yl | 4,843,087 |
| 3-hydroxy | H | 4,5dihydro oxazol-2-yl | 4,843,087 |
| 3,5 di-t-butyl | | 4,5dihydro oxazol-2-yl | 4,843,087 |
| 3-difluoromethyl | H | 4,5dihydro oxazol-2-yl | 4,843,087 |
| 3-hydroxymethyl | H | 4,5dihydro oxazol-2-yl | 4,843,087 |
| 3-carboxy | H | 4,5dihydro oxazol-2-yl | 4,843,087 |
| 2-methyl | 3-hydroxy | 4,5dihydro oxazol-2-yl | 4,843,087 |
| 2,6 dichloro | | 4,5dihydro oxazol-2-yl | 4,843,087 |
| 3,5 difloro | | 4,5dihydro oxazol-2-YI | 4,843,087 |
| 3-chloro | 5-ethynyl | 4,5dihydro oxazol-2-yl | 4,843,087 |

Biological Properties

Biological evaluation of representative compounds of formula I has shown that they possess antipicornaviral activity. They are useful in inhibiting picornavirus replication in vitro and are primarily active against picornaviruses, including enteroviruses, echovirus and coxsackie virus, especially rhinoviruses. The in vitro testing of the representative compounds of the invention against picornaviruses showed that picornaviral replication was inhibited at minimum inhibitory concentrations (MIC) ranging from to micrograms per milliliter (µg/ml).

The MIC values were determined by an automated tissue culture infectious dose 50% (TCID-50) assay. HeLa cells in monoloyers in 96-well cluster plates were infected with a dilution of picornavirus which had been shown empirically to produce 80% to 100% cytopathic effect (CPE) in 3 days in the absence of drug. The compound to be tested was serially diluted through 10, 2-fold cycles and added to the infected cells. After a 3 day incubation at 33° C. and 2.5% carbon dioxide, the cells were fixed with a 5% solution of glutaraldehyde followed by staining with a 0.25% solution of crystal violet in water. The plates were then rinsed, dried, and the amount of stain remaining in the well (a measure of intact cells) was quantitated with an optical density reader. The MIC was determined to be the concentration of compound which protected 50% of the cells from picornavirus-induced CPE relative to an untreated picornavirus control.

In the above test procedures, representative compounds of formula I were tested against some the serotypes from either a panel of fifteen human rhinovirus (HRV) serotypes, (noted in the table as panel T) namely, HRV-2, -14, -1A, -1B, -6, -21, -22, -15, -25, -30, -50, -67, -89, -86 and -41 or against some of the serotypes from a panel of 10 human rhinovirus serotypes, namely HRV-3, -4, -5, -9, -16, -18, -38, -66, -75 and -67, (noted in the table as panel B) and the MIC value, expressed in micrograms per milliliter (mg/ml), for each rhinopicornavirus serotype was determined for each picornavirus, example 1e is given as an example of the data. Then $MIC_{50}$ values, which are the minimum concentrations of the compound required to inhibit 50% of the tested serotypes were determined. The compounds tested were found to exhibit antipicornaviral activity against one or more of these serotypes.

The following Table gives the test results for representative compounds of the invention. The panel of picornaviruses used in the test appears before the the $MIC_{80}$ and $MIC_{50}$ figure and the number of serotypes which the compound is tested against (n) is indicated after the $MIC_{80}$ and $MIC_{50}$ figure.

| Ex | $MIC_{50}$ | n | Panel |
|----|------|----|-------|
| 1e | 0.105 | 14 | T |
| 1g | 6.85 | 15 | T |
| 1h | 0.124 | 13 | T |
| 1i | 37.38 | 8 | T |
| 1j | 51.1 | 2 | T |
| 1k | 0.585 | 15 | T |
| 1l | 49.8 | 2 | T |
| 1m | 0.192 | 7 | T |
| 1n | 33.815 | 12 | T |
| 1f | 19.9 | 1 | T |
| 2b | 0.186 | 9 | B |
| 2c | 50.937 | 8 | B |
| 2d | 0.5 | 4 | B |
| 2e | 3.13 | 9 | B |
| 2f | 0.307 | 8 | B |
| 2a | 69.44 | 10 | B |
| 2h | 0.158 | 10 | B |
| 2i | 0.549 | 8 | B |
| 4c | 0.134 | 8 | B |
| 5e | 0.152 | 9 | B |

Formulations of the Invention

The compounds of formula I can be formulated into compositions, including sustained release compositions together with one or more non-toxic physiologically acceptable carriers, adjuvants or vehicles which are collectively referred to herein as carriers, in any conventional form, using conventional formulation techniques for preparing compositions for treatment of infection or for propylactic use, using formulations well known to the skilled pharmaceutical chemist, for parenteral injection or oral or nasal administration, in solid or liquid form, for rectal or topical administration, or the like.

The compositions can be administered to humans and animals either orally, rectally, parenterally (intravenous, intramuscularly or subcutaneously), intracisternally, intravaginally, intraperitoneally, locally (powders, ointments or drops), or as an aerosal, for example as a nasal or a buccal spray.

Compositions suitable for parenteral injection can comprise physiologically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, polyalkylene glycols and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride and the like. Prolonged absorption of the injectable pharmaceutical form can be brought about by the use of agents that delay absorption, for example, aluminum monostearate and gelatin.

Solid dosage forms for oral administration include capsules, tablets, pills, powders, lozenges and granules which may be dissolved slowly in the mouth, in order to bathe the mouth and associated passages with a solution of the active ingredient. In such solid dosage forms, the active compound is admixed with at least one inert customary excipient (or carrier) such as sodium citrate or dicalcium phosphate or (a) fillers or extenders, as for example, starches, lactose, sucrose, glucose, mannitol and silicic acid, (b) binders, as for example, carboxymethylcellulose, alginates, gelatin, polyvinylpyrrolidone, sucrose and acacia, (c) humectants, as for example, glylcerol, (d) disintegrating agents, as for example, agar-agar, calcium carbonate, potato or tapioca starch, alginic acid, certain complex silicates and sodium carbonate, (e) solution retarders, as for example paraffin, (f) absorption accelerators, as, for example, quaternary ammonium compounds, (g) wetting agents, as for example, cetyl alcohol and glycerol monostearate, (h) adsorbents, as, for example, kaolin and bentonite, and (i) lubricants, as, for example, talc, calcium stearate, magnesium stearate, solid polyethylene glycols, sodium lauryl sulfate or mixtures thereof. In the case of capsules, tablets and pills, the dosage forms can also comprise buffering agents.

Certain solid dosage forms can be delivered through the inhaling of a powder manually or through a device such as a SPIN-HALER used to deliver disodium cromoglycate (INTAL). When using the latter device, the powder can be encapsulated. When employing a liquid composition, the drug can be delivered through a nebulizer, an aerosol vehicle, or through any device which can divide the composition into discrete portions, for example, a medicine dropper or an atomizer.

Solid compositions of a similar type may also be formulated for use in soft and hard gelatin capsules, using such excipients as lactose or milk sugar as well as high molecular weight polyethyleneglycols, and the like.

Solid dosage forms such as tablets, dragees, capsules, pills and granules can be prepared with coatings and shells, such as enteric coatings and others well known in the art. They can contain opacifying agents, and can also be of such composition that they release the active compound or compounds in a certain part of the intestinal tract in a delayed manner.

The active compounds can also be in micro-encapsulated form, if appropriate, with one or more of the above-mentioned excipients.

Liquid dosage forms for oral administration include pharmaceutically acceptable emulsions, solutions, suspensions, syrups and elixirs. Also solid formulations can be prepared as a base for liquid formulations. In addition to the active compounds, the liquid dosage forms can contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, particularly cottonseed oil, ground-nut oil, corn germ oil, olive oil, castor oil and sesame oil, glycerol, tetrahydrofurfuryl alcohol, polyethyleneglycols and fatty acid esters of sorbitan or mixtures of these substances, and the like. Besides such inert diluents, the composition can also include adjuvants, such as wetting agents, emulsifying and suspending agents, sweetening, flavoring and perfuming agents.

Suspensions, in addition to the active compounds, can contain suspending agents, as for example, ethoxylated isostearyl alcohols, polyoxyethylene sorbitol, polyethyleneglycols of varying molecular weights and sorbitan esters, microcrystalline cellulose, aluminum metahydroxide, bentonite, agar-agar and tragacanth, or mixtures of these substances, and the like.

Compositions for rectal or vaginal administration are preferably suppositories which can be prepared by mixing the compounds of the present invention with suitable non-irritating excipients or carriers such as cocoa butter, polyethyleneglycol or a suppository wax, which are solid at ordinary temperatures but liquid at body temperature and, therefore, melt in the rectum or vaginal cavity and release the active component.

Compositions for administration as aerosols are prepared by dissolving a compound of Formula I in water or a suitable solvent, for example an alcohol ether, or other inert solvent, and mixing with a volatile propellant and placing in a pressurized container having a metering valve to release the material in userule droplet size.

The liquefied propellant employed typically one which has a boiling point below ambient temperature at atmospheric pressure. For use in compositions intended to produce aerosols for medicinal use, the liquefied propellant should be non-toxic. Among the suitable liquefied propellants which can be employed are the lower alkanes containing up to five carbon atoms, such as butane and pentane, or a alkyl chloride, such as methyl, ethyl, or propyl chlorides. Further suitable liquefied propellants are the fluorinated and fluorochlorinated alkanes such as are sold under the trademarks "Freon" and "Genetron". Mixtures of the above mentioned propellants can suitably be employed.

Preferred liquefied propellants are chlorine free propellants, for example 134a (tetrafluoroethane) and 227c (heptafluoropropane) which can be used as described above. Typically, one uses a cosolvent, such as an ether, alcohol or glycol in such aerosol formulations.

The specifications for unit dosage forms of this invention are dictated by and directly dependent on (a) the unique characteristics of the active material and the particular effect to be achieved and (b) the limitations inherent in the art of compounding such an active material for use in humans and animals, as disclosed in detail in this specification, these being features of the present invention. Examples of suitable unit dosage forms in accord with this invention are capsules adapted for ingestion or, aerosols with metered discharges, segregated multiples of any of the foregoing, and other forms as herein described.

Compounds of the invention are useful for the prophylaxis and treatment of infections of suspected picornaviral etiologies such as aseptic meningitis, upper respiratory tract infection, enterovirus infections, coxsackievirus, enteroviruses and the like. An effective but non-toxic quantity of the compound is employed in treatment. The dosage of the compound used in treatment depends on the route of administration, e.g., intra nasal, intra bronchial, and the potency of the particular compound.

Dosage forms for topical administration include ointments, powders, sprays and inhalants. The active component is admixed under sterile conditions with a physiologically acceptable carrier and any preservatives, buffers or propellants as may be required. Opthalmic formulations, eye ointments, powders and solutions are also contemplated.

It will be appreciated that the starting point for dosage determination, both for prophylaxis and treatment of picornaviral infection, is based on a plasma level of the compound at roughly the minimum inhibitory concentration levels determined for a compound in the laboratory. For example a MIC of 1 µg/mL would give a desired starting plasma level of 0.1 mg/dl and a dose for the average 70 Kg mammal of roughly 5 mg. It is specifically contemplated that dosage range may be from 0.01–1000 mg.

Actual dosage levels of the active ingredient in the compositions can be varied so as to obtain an amount of active ingredient that is effective to obtain a desired therapeutic response for a particular composition and method of administration. The selected dosage level therefore depends upon the desired therapeutic effect, on the route of administration, on the desired duration of treatment and other factors and is readily determined by those skilled in the art.

The formulation of a pharmaceutical dosage form, including determination of the appropriate ingredients to employ in formulation and determination of appropriate levels of active ingredient to use, so as to achieve the optimum bioavailability and longest blood plasma halflife and the like, is well within the purview of the skilled artisan, who normally considers in vivo dose-response relationships when developing a pharmaceutical composition for therapeutic use.

Moreover, it will be appreciated that the appropriate dosage to achieve optimum results of therapy is a matter well within the purview of the skilled artisan who normally considers the dose-response relationship when developing a regimen for therapeutic use. For example the skilled artisan may consider in vitro minimum inhibitory concentrations as a guide to effective plasma levels of the drug. However, this and other methods are all well within the scope of practice of the skilled artisan when developing a pharmaceutical.

It will be understood that the specific dose level for any particular patient will depend upon a variety of factors including the body weight, general health, sex, diet, time and route of administration, rates of absorption and excretion, combination with other drugs and the severity of the disease being treated and is readily determined by the skilled clinician.

When administered prior to infection, that is, prophylactically, it is preferred that the administration be within about 0 to 48 hours prior to infection of the host animal with the pathogenic picornavirus. When administered therapeutically to inhibit an infection it is preferred that the administration be within about a day or two after infection with the pathogenic virus.

The dosage unit administered will be dependent upon the picornavirus for which treatment or prophylaxis is desired, the type of animal involved, its age, health, weight, extent of infection, kind of concurrent treatment, if any, frequency of treatment and the nature of the effect desired.

The compound of the invention also finds utility in preventing the spread of picornaviral infection the compounds can be used in aerosol sprays applied to contaminated surfaces, to disposable products, such as tissues and the like used by an infected person. In addition the compounds can be used to impregnate household products such as tissues, other paper products, disposable swabs, and the like to prevent the spread of infection by inactivating the picornavirus.

Because compounds of the invention are able to suppress the growth of picornaviruses when added to a medium in which the picornavirus is growing, it is specifically contemplated that compounds of the invention can be used in disinfecting solutions, for example in aqueous solution with a surfactant, to decontaminate surfaces on which polio, Coxsackie, rhinovirus and/or other picornaviruses are present, such surfaces including, but not limited to, hospital glassware, hospital working surfaces, restaurant tables, food service working surfaces, bathroom sinks and anywhere else that it is expected that picornaviruses may be harbored.

Hand contact of nasal mucus may be the most important mode of rhinovirus transmission. Sterilization of the hands of people coming into contact with persons infected with rhinovirus prevents further spread of the disease. It is contemplated that a compound of the invention incorporated into a hand washing or hand care procedure or product, inhibits production of rhinovirus and decreases the likelihood of the transmission of the disease.

We claim:

1. A compound of formula:

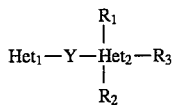

wherein, $Het_1$ is chosen from the group consisting of furyl, oxazolyl, isoxazolyl, oxadiazolyl, tetrazolyl, thiadiazolyl or any of these substituted with alkyl, alkoxy, hydroxy, cycloalkyl, hydroxyalkyl, hydroxyhaloalkyl, alkoxyalkyl, hydroxyalkoxy, alkyl thioalkyl, alkanoyl alkanoyloxy, alkylsulfinyl alkyl, alkylsulfonylalkyl amino alkyl, alkylaminoalkyl, dialkylaminoalkyl, alkoxycarbonyl, carboxy cyanomethyl, fluoroalkyl or halo;

Y is an alkylene bridge of 3 to 9 carbon atoms;

$Het_2$ is quinolyl or quinolyl substituted by $R_1$ and $R_2$;

$R_1$ and $R_2$ are each individually chosen from hydrogen, halo, alkyl, alkenyl, amino, alkylthio, hydroxy, hydroxyalkyl, alkoxyalkyl, alkylthioalkyl, alkylsulfinyl alkyl, alkylsulfonylalkyl, alkoxy, nitro, carboxy, alkoxycarbonyl, dialkylaminoalkyl, alkylaminoalkyl, aminoalkyl, difluoromethyl, trifluoromethyl or cyano;

$R_3$ is alkyltetrazolyl or heterocyclyl chosen from benzoxazolyl, benzathiazolyl, thiadiazolyl, imidazolyl, dihydroimidazolyl, oxazolyl, thiazolyl, oxadiazolyl, pyrazolyl, isoxazolyl, isothiazolyl, furyl, triazolyl, tetrazolyl, thiophenyl or any $R_3$ heterocyclyl above substituted with alkyl, halo, alkoxyalkyl, cycloalkyl, haloalkyl, hydroxyalkyl, alkoxy, hydroxy, furyl, or thienyl or fluoroalkyl the N-oxide thereof or a pharmaceutically acceptable acid addition salt thereof.

2. A compound according to claim 1 wherein $Het_2$ is, quinolyl.

3. A compound according to claim 2 wherein $R_3$ is alkyl tetrazolyl or substituted 1,2,4-oxadiazolyl.

4. A compound according to claim 3 wherein $Het_1$ is isoxazolyl or substituted isoxazolyl.

5. A compound according to claim 4 wherein $R_3$ is 2-methyl-5-tetrazolyl, 5-trifluoromethyl-1,2,4-oxadiazolyl, or 5-methyl-1,2,4-oxadiazolyl.

6. A compound according to claim 5 wherein $R_2$ is hydrogen and $R_1$ is methyl, acetyl, or hydrogen.

7. A pharmaceutical composition containing as an active ingredient an antipicornavirally effective amount of a compound according to claim 1.

8. A pharmaceutical composition containing as an active ingredient an antipicornavirally effective amount of a compound according to claim 3.

9. A pharmaceutical composition containing as an active ingredient an antipicornavirally effective amount of a compound according to claim 5.

10. A pharmaceutical composition containing as an active ingredient an antipicornavirally effective amount of a compound according to claim 6.

11. A method of treating picornaviral infection in a mammalian host comprising administering an antipicornavirally effective amount of a compound according to claim 1.

12. A method of treating picornaviral infection in a mammalian host comprising administering an antipicornavirally effective amount of a compound according to claim 3.

13. A method of treating picornaviral infection in a mammalian host comprising administering an antipicornavirally effective amount of a compound according to claim 5.

14. A method of treating picornaviral infection in a mammalian host comprising administering an antipicornavirally effective amount of a compound according to claim 6.

15. A method of combating picornaviruses comprising contacting the locus of said viruses with a compound of claim 1.

16. A method of combating picornaviruses comprising contacting the locus of said viruses with a compound of claim 3.

17. A method of combating picornaviruses comprising contacting the locus of said viruses with a compound of claim 5.

18. A method of combating picornaviruses comprising contacting the locus of said viruses with a compound of claim 6.

* * * * *